United States Patent [19]

Suciu et al.

[11] Patent Number: 4,503,231

[45] Date of Patent: Mar. 5, 1985

[54] HYDROLYSIS OF NITRILES TO AMIDES WITH QUATERNARY AMMONIUM HYDROXIDE

[75] Inventors: George D. Suciu, Ridgewood; Joon T. Kwon, Freehold Township, Monmouth County, both of N.J.

[73] Assignee: The Lummus Company, Bloomfield, N.J.

[21] Appl. No.: 516,591

[22] Filed: Jul. 25, 1983

[51] Int. Cl.$^3$ .................. C07D 213/82; C07D 213/85; C07B 7/00; C07C 102/08

[52] U.S. Cl. .................................... 546/317; 564/126; 546/169; 546/146; 544/335; 544/224; 544/407; 548/236; 548/248; 548/200; 548/214; 548/343; 548/378; 548/492; 548/537; 549/487; 549/72; 549/425

[58] Field of Search ...................... 546/317, 169, 146; 564/126; 544/335, 224, 407; 548/236, 248, 200, 214, 343, 378, 492, 537; 549/487, 72, 425

[56] References Cited

U.S. PATENT DOCUMENTS 3,670,020 6/1972 Moore ................................. 564/126

FOREIGN PATENT DOCUMENTS 0040896 12/1981 European Pat. Off. ............ 564/126

Primary Examiner—Henry R. Jiles
Assistant Examiner—Dale A. Bjorkman
Attorney, Agent, or Firm—Elliot M. Olstein

[57] ABSTRACT

Hydrolysis of nitrile to amide by use of a quaternary ammonium hydroxide at 60° to 95° C.

16 Claims, No Drawings

HYDROLYSIS OF NITRILES TO AMIDES WITH QUATERNARY AMMONIUM HYDROXIDE

This invention relates to the production of amides, and more particularly, to a new and improved process for producing amides from nitriles.

The present invention is most particularly directed to the production of nicotinamide from nicotinonitrile.

The conversion of nitriles to amides by a hydrolysis reaction is known in the art. Thus, for example, U.S. Pat. No. 4,008,241 describes conversion of nicotinonitrile to nicotinamide by the use of ammonia as a catalyst.

U.S. Pat. No. 4,314,064 describes a process for conversion of nicitononitrile to nicotinamide by hydrolysis in the presence of alkali hydroxides.

In using sodium hydroxide as a catalyst, at higher conversions, selectivity to nitrile is reduced. In addition, additional sodium hydroxide is difficult to remove from the final product.

In using ammonia as a catalyst, in general, selectively is reduced at higher conversions. In addition, longer reaction times and higher temperature are required.

In accordance with one aspect of the present invention, there is provided a process for hydrolyzing a nitrile to an amide wherein the hydrolysis is effected in the presence of a catalytically effective amount of a quaternary ammonium hydroxide. Applicant has found that by using a quaternary ammonium hydroxide as a catalyst in the hydrolysis of nitrile to amide, there can be achieved a reduction in reaction time, while maintaining high conversion and selectivity to the amide, i.e., the hydrolysis can be selectively accomplished so as to minimize production of the acid.

The quaternary ammonium hydroxide which may be employed as a catalyst for hydrolysis of nitrile to amide may be represented by the following structural formula:

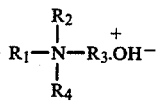

wherein each of $R_1$, $R_2$, $R_3$ and $R_4$ are either alkyl or phenyl substituted alkyl wherein the phenyl group may be unsubstituted or substituted with an alkyl group. It is to be understood that $R_1$, $R_2$, $R_3$ and $R_4$ may be different groups or may be the same. In the preferred compounds, each of $R_1$, $R_2$, $R_3$ and $R_4$ is alkyl, preferably an alkyl group having from one to 16 carbon atoms, with each of $R_1$, $R_2$, $R_3$ and $R_4$ most preferably being the same alkyl group.

The quaternary ammonium hydroxide is employed in the reaction mixture in a catalytically effective amount. In most cases, the quaternary ammonium hydroxide is not present in an amount of less than 0.1 mole per mole of nitrile in that lower amounts would increase the overall reaction time. In most cases, the quaternary ammonium hydroxide is not employed in an amount in excess of about 2 moles per 100 moles of nitrile in that amounts in excess of such value would not be economically justified. It is to be understood, however, that a higher amount could be employed.

The hydrolysis is generally effected at a temperature between the freezing point and the boiling point of the mixture at the operating pressure. Thus, for example, at atmospheric pressures, the hydrolysis preferably is accomplished at a temperature in the order of from 60° C. to 95° C. It is to be understood, however, that the reaction may be accomplished at pressures other than atmospheric pressures, including sub-and super-atmospheric pressures. The pressure is preferably one at which most of the reaction mixture is in the liquid phase at the reaction temperature.

The nitrile concentration in the initial water nitrile mixture can vary over a wide range. As should be apparent, water should be present in an amount which is at least sufficient to provide the desired conversion of nitrile. The nitrile concentration in the water is preferably one at which the liquid phase is homogeneous at the reaction temperature. In most cases, the nitrile concentration is in the order of from 15 to 85 percent, preferably from 55 to 75% by weight, based on water and nitrile.

The hydrolysis of nitrile to amide in the presence of the quaternary ammonium hydroxide may be accomplished without the use of a diluent or solvent, provided that there is sufficient miscibility between the nitrile and the water. In the event that there is not sufficient miscibility, a water miscible solvent (for example, an alcohol) may be used so as to increase miscibility. If the nitrile is normally a solid, the nitrile may be dissolved in a suitable solvent, such as a hydrocarbon. The selection of a suitable solvent, if required, is deemed to be within the scope of those skilled in the art from the teachings herein.

The use of a quaternary ammonium hydroxide as a catalyst for conversion of nitrile to amide permits high conversion while retaining high selectivity at short reaction times; e.g., nicotinonitrile can be hydrolyzed at conversions up to about 90% in times of less than 60 minutes (for example, in times as short as 2–5 minutes) while maintaining selectivity over 90% and in particular, in excess of 95%.

A further advantage of employing a quaternary ammonium hydroxide as a catalyst for conversion of a nitrile to the corresponding amide is that the catalyst can be easily removed from the reaction effluent so as to obtain an amide product of higher purity.

Thus, for example, the quaternary ammonium hydroxide may be easily removed from the reaction effluent by the use of ion exchange resins, and in particular, acid ion exchange resins. The selection of a suitable ion exchange resin for removing quaternary ammonium hydroxide is deemed to be within the scope of those skilled in the art from the teachings herein. The procedure offers the further advantage that the quaternary ammonium hydroxide can be recovered from the ion exchange resin for reuse in the hydrolysis reaction.

In accordance with another procedure, the quaternary ammonium hydroxide may be distilled from the reaction effluent. In such a procedure, the quaternary ammonium hydroxide is distilled from the effluent along with any unreacted nitrile and some water, whereby the unreacted nitrile and quaternary ammonium hydroxide may be simultaneously recycled to the hydrolysis reaction. A particularly preferred quaternary ammonium hydroxide is tetra-butyl ammonium hydroxide in that such compound is stable at elevated temperatures, whereby the compound may be distilled from the reaction effluent without significant losses thereof.

The present invention is applicable to the hydrolysis of a wide variety of nitriles to amides, including the hydrolysis of aliphatic nitriles, aromatic nitriles, and heterocyclic nitriles.

As representative examples of suitable aromatic nitriles, there may be mentioned cyano substituted benzenes and cyano substituted naphthalenes which contain one or more cyano groups, such as benzonitrile, phthalonitrile, etc.

As representative examples of suitable aliphatic nitriles, there may be mentioned cyano substituted furans, pyrroles, indoles, thiophenes, pyrazoles, imidazoles, thiazoles, oxazoles, pyrans, pyridines, quinolines, isoquinolines, pyramidines, pyrimidines, pyridazines, pyrazines, etc. The preferred heterocyclic compounds are cyano substituted pyridines, and in particular, nicotinonitrile.

The invention will be further described with respect to the following examples; however, the scope of the invention is not to be limited thereby:

EXAMPLES 1-5

In a series of batch tests the hydrolysis was carried out with varying ratios of tetramethyl-ammonium hydroxide (TMAH)/nicotinonitrile (NN). All tests were carried out at 60° C., starting with an initial nicotinonitrile concentration in water of 33.3 mole % (74.2wt%).

Results are given in Table 1.

Analyses were preformed by GC, for the NN and water and by HPLC for the nicotinamide and nicotinic acid.

TABLE 1

| Example No. | TMAH/NN m/100 moles | NN Conversion (%) at Various Times (min) | | | | Select. to Amide After 60 min. Mole % |
|---|---|---|---|---|---|---|
| | | 15 | 30 | 45 | 60 | |
| 1 | 0.1 | 30.7 | 34.9 | 36.7 | 42.8 | 94.0 |
| 2 | 0.25 | 35.5 | 42.9 | 46.1 | 52.2 | 97.4 |
| 3 | 0.50 | 35.6 | 44.1 | 56.4 | 58.3 | 92.0 |
| 4 | 1.0 | 71.6 | 75.3 | 77.7 | 78.9 | 98.0 |
| 5 | 2.0 | 80.1 | 81.9 | 85.5 | 86.8 | 97.4 |

EXAMPLES 6-7

In conditions similar to those of Example 4, the catalytic activity was tested for tetraethyl-(TEAH), and tetrabutyl-ammonium hydroxide (TBAH) at 1 mole/100 moles NN ratio. Table 2 contains the results.

TABLE 2

| Example No. | Catalyst | NN Conversion (%) at Various Times (min) | | | | Select. to Amide After 60 min. Mole % |
|---|---|---|---|---|---|---|
| | | 15 | 30 | 45 | 60 | |
| 6 | TEAH | 63.2 | 70.6 | 73.9 | 74.0 | 97.7 |
| 7 | TBAH | 62.5 | 68.6 | 72.9 | 75.2 | 97.1 |

EXAMPLES 8-10

The effect of the NN concentration was investigated in batch system at 60° C. with 1 mole TMAH/100 moles NN. The results are recorded in Table 3.

TABLE 3

| Example No. | Initial NN Conc. | | NN Conv. (%) at Various Times (min) | | | | Select to Amide After 60 min. Mole % |
|---|---|---|---|---|---|---|---|
| | Wt % | Mole % | 15 | 30 | 45 | 60 | |
| 8 | 40 | 10.5 | 47.7 | 63.6 | 69.6 | 73.2 | 95.4 |
| 9 | 57.1 | 15.8 | — | 65.6 | — | 77.6 | 97.1 |
| 4 | 74.2 | 33.3 | 71.6 | 75.3 | 77.7 | 78.9 | 98.0 |
| 10 | 83.3 | 45.0 | 50.6 | 58.2 | 55.1 | 61.0 | 96.8 |

EXAMPLES 11-14

The hydrolysis of NN was performed in a continuous manner. The reactor consisted of a stainless steel coil maintained at 95° C. Conditions approaching those of a plug-flow reactor prevailed.

A solution of NN in variable amounts of water was mixed with a 20 wt% solution of TMAH in water so as to achieve a ratio TMAH/NN of 1/100 molar. Samples were collected so as to represent steady state in various operating conditions.

In order to avoid flashing, a system pressure of 1-2 atm. was maintained. The results are reported in Table 4. Residence times are calculated on the basis of total volume flow rate.

TABLE 4

| Example No. | Conc of NN in Feed (Wt %) | TMAH/NN (mol/100 mole) | Residence Time (min) | NN Conversion | Selectivity to Amide Mole % |
|---|---|---|---|---|---|
| 11 | 49.1 | 0.72 | 4.9 | 67.9 | 99.3 |
| 12 | 76.3 | 1.10 | 2.6 | 62.7 | 95.7 |
| 13 | 74.4 | 0.92 | 4.7 | 84.2 | 97.5 |
| 14 | 74.4 | 1.06 | 4.8 | 87.1 | 98.1 |

EXAMPLE 15

The catalyst can be efficiently recovered from the reaction mixture by use of ion exchangers.

A cation exchanger such as Dowex 50X8 in the H-form (1.7 meq/g) was used for retaining the TMAH from samples collected from the reactor effluent of Experiment 14 above.

To samples of 30 ml hydrolysis product maintained at 45±5° C. and containing 1.47 meq TMAH, various amounts of resin were added and stirred for a few minutes. The resin was separated by filtration and the pH of the filtrate was measured. For 0, 0.5, 1.0, and 2.0 g of resin added to each of four 30 ml hydrolysis product, the pH of the filtrates was 10.3, 8.7, 6.1, and 5.1, respectively. For comparison, the aqueous nitrile feed has pH=8.7 and a concentrated aqueous solution of reagent grade nicotinamide has pH=6.6, at the same temperature.

EXAMPLE 16

A preferred method for recovering the catalyst from the reactor effluent is by distillation.

Effluent from the hydrolysis reactor 463 g, containing (wt%) nicotinamide 48.6%, unreacted NN 7.3%, nicotinic acid 0.6%, TBAH 1.2% (ca. 41 meq/l.) and the balance water, were introduced into a distillation flash provided with a 1" ID distillation column which had 10 actual trays. The distillation was carried out batchwise, at atmospheric pressure, with a reflux ratio of appxoximately 1.1. Distillate cuts were collected and analyzed for TBAH. All distillates consisted of water, TBAH and NN only. The results of the test are presented in Table 5.

TABLE 5

| Distillate (% wt of charge) | TBAH Recovered (% of charged) Cumulative | Conc. TBAH in Overhead (meq/g) | Temperature (°C.) Overhead | Bottoms |
|---|---|---|---|---|
| 1 | 73.9 | 2.86 | 99 | 104 |
| 3 | 90.4 | 0.35 | 99–100 | 105 |
| 5 | 97.2 | 0.14 | 99–100 | 105 |
| 7 | 100.0 | 0.09 | 99–100 | 105 |

The above results demonstrate the ability to recover completely TBAH from the reactor effluent by distillation. Since the concentration of the TBAH in the distillate is high, it can be recycled as such to the hydrolysis reactor.

EXAMPLE 17

The method of the present patent was applied to the hydrolysis of benzonitrile (BN). The various reagents were introduced into a batch reactor so as to obtain the molar ratio TMAH/H$_2$O/BN equal to 4.9/420/100. At 60° C., the conversion of the BN obtained after 30, 60, and 120 minutes were 8.9, 20.5 and 29.6 mole % respectively.

EXAMPLE 18

In the condition of Example 17, the TMAH/H$_2$O/BN nole ratio were 2.2/850/100. In order to have a homogeneous liquid phase, ethanol was added. The concentrations of BN and H$_2$O in the initial homogeneous mixture were 29 and 43% wt., respectively. The conversion of BN after 30, 60 and 120 minutes were 9.9, 13.3 and 30.1%, respectively.

The present invention is particularly advantageous, in that it permits conversion of nitrile to amide, and in particular, nicotinonitrile to nicotinamide, in short reactions times, at high conversions, and with high selectivity to amide. Thus, for example, it is possible to achieve conversions in the order of from 60% to 90% amide, selectivities in the order of from 95% to 99%, at reaction times of less than 60 minutes, in particular, in the order of from 2 to 5 minutes.

In addition, the catalyst may be easily removed from the reaction effluent, thereby producing a final product of higher purity. This is particularly advantageous in the conversion of nicotinonitrile to nicotinamide in that nicotinamide is used as fodder or as human food additive.

These and other advantages should be apparent to those skilled in the art from the teachings herein.

Numerous modifications and variations of the present invention are possible in light of the above teachings and, therefore, within the scope of the appended claims, the invention may be practiced otherwise as particularly described.

What is claimed is:

1. In a process for hydrolyzing a nitrile to an amide, the improvement comprising:
    effecting said hydrolysis of a nitrile to an amide with water at a temperature of from 60° C. to 95° C. in the presence of a catalytically effective amount of a catalyst consisting essentially of a quaternary ammonium hydroxide.

2. The process of claim 1 wherein the quaternary ammonium hydroxide is a tetraalkyl quaternary ammonium hydroxide.

3. The process of claim 2 wherein the quaternary ammonium hydroxide is present in an amount of at least 0.1 mole per mole of nitrile.

4. The process of claim 3 wherein the reaction time is less than 60 minutes.

5. The process of claim 4 wherein the conversion of nitrile is from 60% to 90%.

6. The process of claim 3 wherein the quaternary ammonium hydroxide is tetrabutyl ammonium hydroxide.

7. The process of claim 6 and further comprising distilling hydrolysis effluent to separate quaternary ammonium hydroxide, unreacted nitrile and any water from amide product.

8. In a process for hydrolyzing nicotinonitrile to nicotinamide, the improvement comprising:
    effecting said hydrolysis of nicotinonitrile to nicotinamide with water at a temperature of from 60° C. to 95° C. in the presence of a catalytically effective amount of a catalyst consisting essentially of a quaternary ammonium hydroxide.

9. The process of claim 8 wherein the quaternary ammonium hydroxide is a tetraalkyl quaternary ammonium hydroxide.

10. The process of claim 9 wherein the quaternary ammonium hydroxide is present in an amount of at least 0.1 mole per mole of nitrile.

11. The process of claim 10 wherein the reaction time is less than 60 minutes.

12. The process of claim 11 wherein the conversion of nitrile is from 60% to 90%.

13. The process of claim 10 wherein the quaternary ammonium hydroxide is tetrabutyl ammonium hydroxide.

14. The process of claim 13 and further comprising distilling hydrolysis effluent to separate quaternary ammonium hydroxide, unreacted nitrile and any water from amide product.

15. The process of claim 12 wherein the selectivity to nicotinamide is in excess of 95%.

16. The process of claim 15 wherein the reaction time is from 2–5 minutes.

* * * * *